United States Patent [19]
Minns et al.

[11] Patent Number: 5,723,016
[45] Date of Patent: Mar. 3, 1998

[54] IMPLANTABLE PROSTHETIC PATELLAR COMPONENTS

[75] Inventors: Julian Richard Minns, Durham; Swee Chai Ang, London; Ian Wiliam Wallace, Tyne & Wear, all of England

[73] Assignee: British Technology Group Ltd., London, England

[21] Appl. No.: 530,153

[22] PCT Filed: Mar. 31, 1994

[86] PCT No.: PCT/GB94/00701

§ 371 Date: Nov. 17, 1995

§ 102(e) Date: Nov. 17, 1995

[87] PCT Pub. No.: WO94/22397

PCT Pub. Date: Oct. 13, 1994

[30] Foreign Application Priority Data

Apr. 1, 1993 [GB] United Kingdom ............ 9306898

[51] Int. Cl.[6] .................................... A61F 2/38
[52] U.S. Cl. .................................. 623/20; 612/18
[58] Field of Search .................... 623/16, 18, 20

[56] References Cited

U.S. PATENT DOCUMENTS

| | | |
|---|---|---|
| 4,007,495 | 2/1977 | Frazier . |
| 4,041,550 | 8/1977 | Frazier . |
| 4,151,615 | 5/1979 | Hall . |
| 5,246,460 | 9/1993 | Goodfellow et al ............ 623/20 |

FOREIGN PATENT DOCUMENTS

| | | |
|---|---|---|
| 038896 | 11/1981 | European Pat. Off. . |
| 91 16 507 | 12/1992 | Germany . |
| 92/03109 | 3/1992 | WIPO . |
| 93/00871 | 1/1993 | WIPO . |

Primary Examiner—Randy C. Shay
Attorney, Agent, or Firm—Cushman, Darby & Cushman IP Group of Pillsbury Madison & Sutro LLP

[57] ABSTRACT

An implantable prosthetic patellar component comprises a patellar part (1) having one side (1a) adapted to be secured to the inner surface of a natural patella (10), and a femoral part (3) having one side (5) defining an articulation surface to replace the femoral facet of the patella, the opposite surfaces (1b and 3a) of said parts being mutually engageable to afford sliding movement therebetween in a medio-lateral direction.

The implant is able to accommodate relative medio-lateral movement and thereby improve congruency. It may be used in combination with other prosthetic components in a knee joint.

8 Claims, 2 Drawing Sheets

IMPLANTABLE PROSTHETIC PATELLAR COMPONENTS

This invention concerns prosthetic patellar components for implantation in the knee joint of a patient.

A number of different knee prostheses have been developed for surgical treatment of the disabling effects of knee joint deterioration, such as results from arthritis, injury or disease. A fairly common operation nowadays is total knee replacement, where the femoral facets of the proximal tibia as well as the patellar and tibial facets of the distal femur are replaced with prosthetic components. It is also recognised that replacing the articulating surface on the posterior aspect of the patella improves the result of such operations, and prosthetic patellar elements for such a purpose have been developed.

More recently study has been carried out directed to investigation of contact stresses between the patella and the femoral components in three common designs of knee prostheses. At different angles of flexion under a load of 500 newtons contact stresses across the patello-femoral interface were monitored. It was determined from these tests that the contact stress areas move outwards towards the periphery of the interface and the contact stress values increase at increases in knee flexion, for all the designs tested. patellar implants retrieved at revision of the designs tested confirmed wear and deformation in the areas of measured maximum contact stress. All the designs showed poor congruency at all angles of knee flexion.

Examples of prosthetic patellar components are disclosed in DE-U-9116507.5, WO-93/00871 and U.S. Pat. No. 4,041,550. None of these teachings provides a device which suitably accommodates the conditions referred to above.

To improve this situation the present invention provides a novel implantable prosthetic patellar component, comprising a patellar part having one side adapted to be secured to the inner surface of a natural patella, and a femoral part having one side defining an articulation surface to replace the femoral facet of the patella, the opposite sides of said parts being mutually engageable to afford sliding movement therebetween in a medio-lateral direction.

The invention therefore provides an implantable prosthetic patellar component of two-part form, these two parts of the component referred to herein as the patellar part and the femoral part. When in place in a patient the component according to the invention allows sliding movement between the two parts in the medio-lateral direction to accommodate naturally occurring relative movement in this direction. Considerable variation in the quadriceps-patellar ligament angle from subject to subject produces variations in the magnitude of the medio-lateral force acting on the patella, and such variations are allowed for by the component of the present invention. This improves congruency throughout flexion and at various loading of the joint, which has the effect of considerably reducing wear and deformation by reducing contact stresses during movement of the joint.

In a preferred form, the engagement between the two parts allows translational sliding movement only in a substantially medio-lateral direction. In this way, sliding displacement of the whole of one part relative to the other part is limited to that in a substantially medio-lateral direction.

Preferably, either the patellar part or the femoral part has an elongated dovetail slot, the other part having a complementary projection, such as a dovetail rib or a flared stud, the slot and the projection being dimensioned for engagement to afford the sliding movement between the two parts. In this way, the mutually interfacing sides of the parts are held in contact and the risk of dislocation of one part from the other is reduced. The provision of a flared stud accomplishes this whilst at the same time allowing relative rotation about an axis in the anterio-posterior direction.

Certain embodiments of the invention will now be described by way of example with reference to the accompanying drawings, in which.

Figures 1A, 1B:
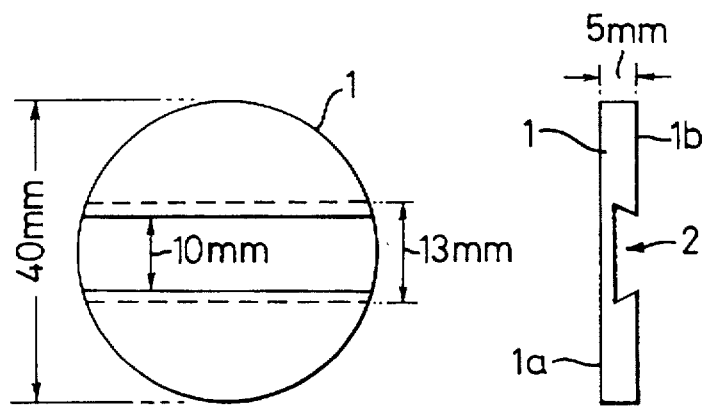
FIGS. 1a and 1b illustrate a patellar part of a prosthetic patellar component according to the invention.

The patellar part of the illustrated patellar component consists of a metal disc 1 with a planar fixation on surface 1a for attachment to an inner surface of a natural patella, and an opposite parallel planar interface surface 1b in which a dovetail slot 2 is machined. FIG. 1a shows a plan view of the part, whilst FIG. 1b shows a side elevation.

Figures 2A, 2B, 2D:
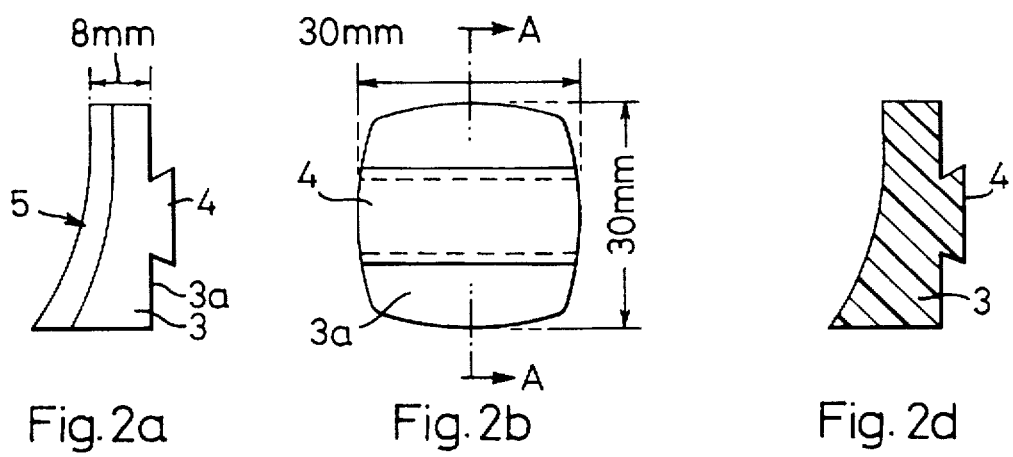
FIGS. 2a to 2d illustrate a femoral part of such a component.
Figure 2C:
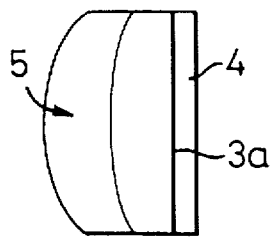

The femoral part of the patellar component is shown FIG. 2, where FIG. 2a offers a side elevation of the part, FIG. 2b offers a front view, FIG. 2c offers a top view, and FIG. 2d offers a cross section of the part across plane A—A of FIG. 2b.

The femoral part consists of an articulation element 3 of suitable biocompatible material, such as ultrahigh molecular weight polyethylene, having a planar interface surface 3a, from which a dovetail rib 4 protrudes, this rib being complementary to the dovetail slot 2 in the patellar part so that when inter-engaged the two can slide smoothly relative to one another in a direction parallel to the slot.

The opposite side of the femoral part consists of a smooth articulation facet 5 which, as can be seen from FIGS. 2a and 2c, is concavely curved in one direction and convexly curved in a perpendicular direction giving the part a 'saddle-shaped' bearing surface. The actual curvatures in both directions will depend on the shape of the corresponding surface of the femoral component against which the part is designed to articulate, this last shape —the patellar facet —commonly being that of a trough. The side edges of the part are rounded as can be seen in FIG. 2b. Example dimensions for the two parts of the component are given in the figures but clearly can be varied in practice to suit different requirements.

Figure 3:
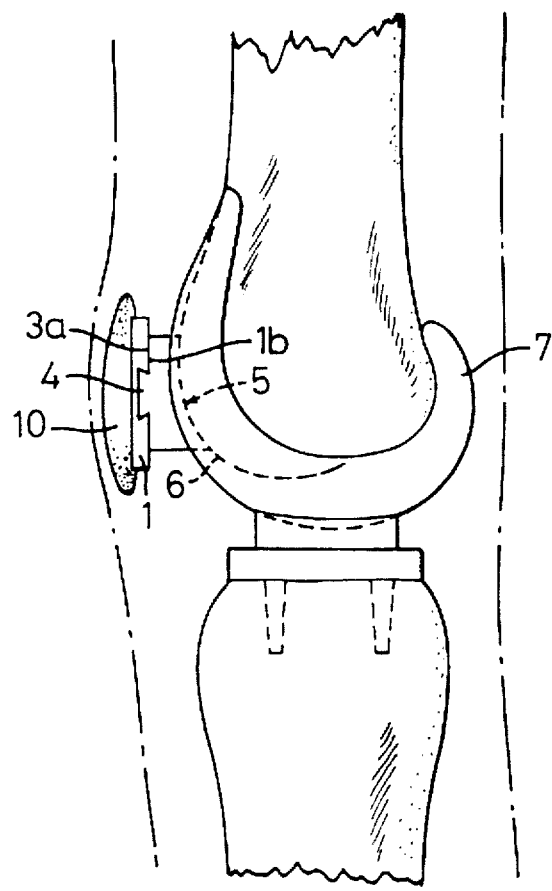
FIG. 3 represents in side elevation a total knee replacement incorporating the patellar component illustrated FIGS. 1 and 2.

The operation of the parts of the component when implanted in a patient's knee will now be described with reference to FIG. 3. This shows the patellar component used in a total knee replacement, but it is to be understood that the component could be used as a sole implant, functioning in an otherwise natural joint.

The inner surface of the patient's patella 10 is appropriately prepared by a surgeon for fixation to the planar fixation surface of the patellar part 1 and the two are connected together such that the dovetail slot 2 is arranged in the medio-lateral direction. The fixation may be by means of bone cement and/or fixation pins, or alternatively a projecting stud (not shown) may be provided on the fixation surface of the patellar part to facilitate satisfactory fixation. The femoral part 3 is then engaged with the patellar part by means of the dovetail slot 2 and complementary rib 4, and the articulation facet 5 is brought into contact with the patellar facet 6 of the femoral component 7. When in place, the articulation facet 5 has a concave sagittal profile and a convex transverse profile a convex profile when viewed in superior aspect).

In subsequent flexion of the joint, the articulation facet 5 moves against the patellar facet of the femoral component 7, guided in this trough-shaped surface by virtue of the convex transverse profile of its bearing surface. At the same time, the lateral pull during flexion found in the knee joint and described above is accommodated by a sliding motion between the two parts of the component in the medio-lateral direction. The polyethylene articulation element 3 tracks from side to side by means of the dovetail joint, the planar surfaces 1b and 3a thus sliding smoothly over one another, and this tracking allows increased congruency throughout flexion and at different loads on the joint.

Figure 4A:
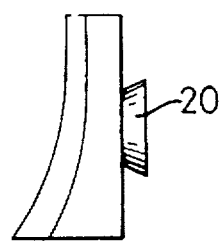
FIGS. 4a and 4b illustrate an alternative form of a femoral part of the component.
Figure 4B:
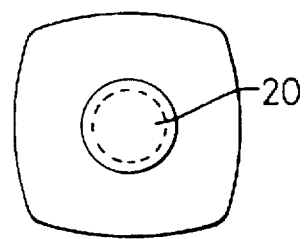

When the patellar component has been implanted it can be difficult to ensure that the articulation facet at the back of the component will conform with the patellar facet of the femoral component, depending partly on the accuracy of the fixation of the component to the natural patella. For this reason it is beneficial to build into the design the ability to permit rotation in a coronal plane. FIGS. 4a and 4b (which present similar views to those in FIGS. 2a and 2b) illustrate a femoral part which allows both rotation and sliding between the two parts of the component. In place of the dovetail rib 4 a central flared stud 20 projects from the planar interface surface. When this stud is engaged in the dovetail slot 2 of the patellar part of the component the two parts can move relative to one another both by sliding in a direction parallel to the slot and by rotation about the stud, and when implanted this design provides, in certain situations, further improved congruency within the joint.

Whilst the invention has been described and illustrated in conjunction with specific embodiments thereof, it should be understood that this in no way limits the scope of the invention, which is intended to embrace all other embodiments that fall within the spirit and scope of the appended claims.

We claim:

1. An implantable prosthetic patellar component comprising a patella part having a first side adapted to be secured to an inner surface of a natural patella, and a femoral part having a first side defining an articulation surface to replace the femoral face of the patella and slide freely relative to a femur, each of said parts having a second side, said second sides being mutually engageable to afford sliding movement therebetween in a medio-lateral direction.

2. A component according to claim 1, wherein the two parts are engageable for translational sliding movement therebetween only in a substantially medio-lateral direction.

3. A component according to claim 2, wherein either the patella part or the femoral part has a longitudinal dovetail slot, and the other part has a complementary projection, the slot and the projection being dimensioned for engagement to afford said sliding movement between the two parts.

4. A component according to claim 3, wherein the projection is a dovetail rib.

5. A component according to claim 3, wherein the projection is a flared stud.

6. A component according to claim 1, wherein the articulation surface of the femoral part has a concave sagittal profile.

7. A component according to claim 1, wherein the articulation surface of the femoral part has a convex transverse profile.

8. A component according to any one of claims 1 to 7, wherein the mutually engageable surfaces of the two parts are substantially planar.

* * * * *